US012758413B2

(12) United States Patent
Baytos

(10) Patent No.: US 12,758,413 B2
(45) Date of Patent: Oct. 13, 2026

(54) GARMENT FOR POSTURE PROMOTION

(71) Applicant: Pro-NMT, Inc., Beverly Hills, CA (US)

(72) Inventor: Barrence Baytos, El Segundo, CA (US)

(73) Assignee: Pro-NMT, Inc., Beverly Hills, CA (US)

( * ) Notice: Subject to any disclaimer, the term of this patent is extended or adjusted under 35 U.S.C. 154(b) by 205 days.

(21) Appl. No.: 18/386,223

(22) Filed: Nov. 1, 2023

(65) Prior Publication Data

US 2024/0139016 A1 May 2, 2024

Related U.S. Application Data

(60) Provisional application No. 63/421,321, filed on Nov. 1, 2022.

(51) Int. Cl.
*A61F 5/02* (2006.01)
*A41D 31/18* (2019.01)

(52) U.S. Cl.
CPC ................ *A61F 5/02* (2013.01); *A41D 31/18* (2019.02)

(58) Field of Classification Search
CPC .. A61F 5/02; A61F 5/026; A61F 5/028; A61F 5/03; A61F 5/30; A61F 2005/0197;
(Continued)

(56) References Cited

U.S. PATENT DOCUMENTS

| | | | | |
|---|---|---|---|---|
| 1,386,067 A * | 8/1921 | Mason | .................... | A61F 5/026 2/45 |
| 6,159,070 A * | 12/2000 | Schwartz | ................. | A41C 1/10 450/155 |

(Continued)

FOREIGN PATENT DOCUMENTS

| | | | | |
|---|---|---|---|---|
| EP | 1588638 A1 * | 10/2005 | ............. | A41D 15/00 |
| WO | WO-2004091328 A1 * | 10/2004 | ............. | A41D 31/18 |

OTHER PUBLICATIONS

EP-1588638-A1 translated (Year: 2005).*
WO-2004091328-A1 translated (Year: 2004).*

*Primary Examiner* — Alireza Nia
*Assistant Examiner* — Michael Milo
(74) *Attorney, Agent, or Firm* — Foundation Law Group LLP; JD Harriman; Sevag Demirjian

(57) ABSTRACT

A garment for supporting posture of an individual includes a form-fitting portion. The form-fitting portion includes an upper and lower body section each having an interior and exterior surface area. A support structure includes an elastomeric band body and is affixed to the exterior surface area of the form-fitting portion. The support structure is positioned on an upper and lower body section of the form-fitting portion. A method of forming a garment for supporting posture of an individual includes providing a form-fitting portion having upper and lower body sections, where each of the upper and lower body sections have interior and exterior surface areas. A support structure is affixed to the exterior surface area of the form-fitting portion, where the support structure includes an elastomeric band body and is positioned on an upper body section and a lower body section of the form-fitting portion.

19 Claims, 9 Drawing Sheets

(58) Field of Classification Search
CPC .. A61F 13/148; A61F 13/00038; F16D 13/58; A61B 5/389; A61H 2201/1602; A41C 1/08; A41D 13/18
USPC .............................................................. 602/1
See application file for complete search history.

(56) References Cited

U.S. PATENT DOCUMENTS

| | | | | |
|---|---|---|---|---|
| 2013/0160189 | A1* | 6/2013 | Yang | A63B 21/4011<br>2/227 |
| 2015/0313295 | A1* | 11/2015 | Bye | A41D 13/02<br>2/456 |
| 2017/0347720 | A1* | 12/2017 | Gehlhausen | A41B 9/08 |
| 2019/0358074 | A1* | 11/2019 | Zelik | A61B 5/389 |
| 2022/0346469 | A1* | 11/2022 | Minakuchi | A41D 7/00 |

* cited by examiner

GARMENT FOR POSTURE PROMOTION

CROSS-REFERENCE TO RELATED APPLICATIONS

This application claims priority from U.S. Provisional Patent Application No. 63/421,321, filed Nov. 1, 2022, and entitled "GARMENT FOR POSTURE PROMOTION," the entire disclosure of which is incorporated herein by reference.

FIELD OF THE INVENTION

The disclosure relates generally to garments, and more specifically to garments for promoting beneficial postural aspects of an individual.

BACKGROUND

Posture is something that many individuals struggle with on a daily basis. In a world where many individuals' bodies are affected by their daily work and phone habits, proper/beneficial posture habits are typically an afterthought. Areas of the body that are typically affected include regions of the body such as the neck, shoulders, back, hips, knees, and upper and lower extremities.

One population of individuals that can greatly benefit from having proper posture includes athletes. Athletes must be in peak physical condition in order for them to perform optimally at their sport, which implies that their bodies must be in optimal shape. Proper posture plays a key role in the health and optimal performance of the body. Additional populations of individuals that can benefit from proper posture include pregnant women, individuals that work on computers, and physical laborers. The weight of a child as well as any unnatural positioning of the body in relation to work may pose a threat to proper posture of an individual.

SUMMARY OF THE INVENTION

According to an embodiment of the present disclosure, a garment for supporting posture of an individual includes a form-fitting portion having an upper body section and a lower body section. Each of the upper body section and the lower body section have an interior surface area and an exterior surface area. The garment additionally includes a support structure comprising an elastomeric band body and is affixed to the exterior surface area of the form-fitting portion and positioned on an upper body section and a lower body section of the form-fitting portion.

According to an embodiment of the present disclosure, a method of forming a garment for supporting posture of an individual includes providing a form-fitting portion including an upper body section and a lower body section, where each of the upper body section and the lower body section have an interior surface area and an exterior surface area. A support structure is then affixed to the exterior surface area of the form-fitting portion, where support structure includes an elastomeric band body and is positioned on an upper body section and a lower body section of the form-fitting portion.

BRIEF DESCRIPTION OF THE DRAWINGS

The drawings are of illustrative embodiments. They do not illustrate all embodiments. Other embodiments may be used in addition or instead. Details that may be apparent or unnecessary may be omitted to save space or for more effective illustration. Some embodiments may be practiced with additional components or steps and/or without all of the components or steps that are illustrated. When the same numeral appears in different drawings, it refers to the same or like components or steps.

DETAILED DESCRIPTION

Reference now should be made to the drawings, in which the same reference numbers are used throughout the different figures to designate the same components.

It will be understood that, although the terms first, second, third, etc. may be used herein to describe various elements, these elements should not be limited by these terms. These terms are only used to distinguish one element from another element. Thus, a first element discussed below could be termed a second element without departing from the teachings of the present disclosure.

The terminology used herein is for the purpose of describing particular embodiments only and is not intended to be limiting. As used herein, the singular forms "a", "an", and "the" are intended to include the plural forms as well, unless the context clearly indicates otherwise. It will be further understood that the terms "comprises" and/or "comprising" or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

For the purposes of this disclosure, it is noted that beneficial postural aspects of an individual can include any of the following: keeping the individual's head in line with their body and level, standing up straight with the individual's shoulders drawn down and back, keeping the individual's feet apart at shoulder width, pulling in the individual's abdomen, tucking down the individual's rib cage with neutral hips, and putting the individual's weight mainly on the balls of the feet. This list is non-exhaustive and can include other aspects in addition to the aspects listed above.

Figure 1C:
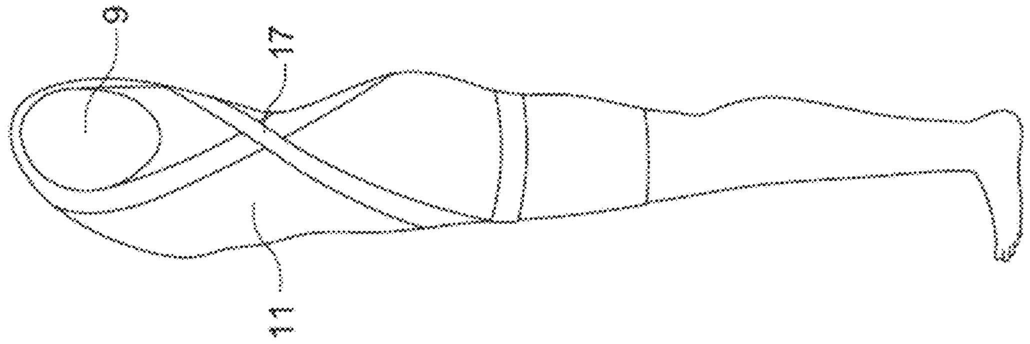
FIG. 1C displays a side view of a short-legged garment for supporting posture of an individual in accordance with embodiments.
Figure 1B:
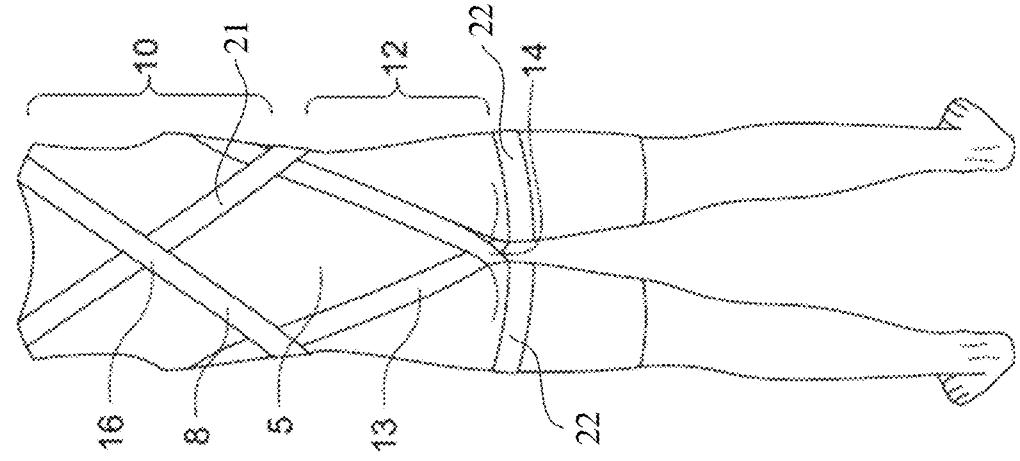
FIG. 1B displays a rear view of a short-legged garment for supporting posture of an individual in accordance with embodiments.
Figure 1A:
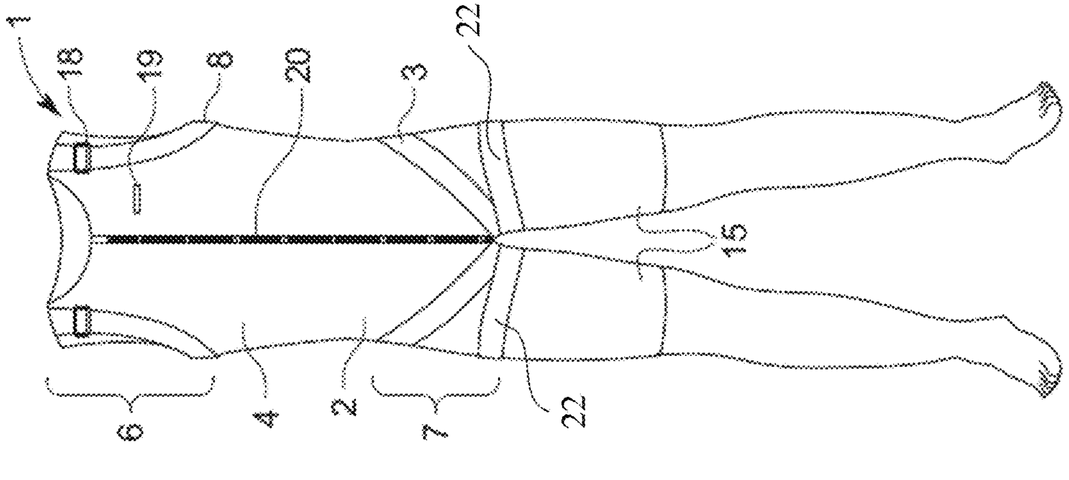
FIG. 1A displays a front view of a short-legged garment for supporting posture of an individual in accordance with embodiments.

FIG. 1A displays a front view of a short-legged garment 1 for supporting posture of an individual in accordance with embodiments. Garment 1 may be configured to assist an individual in propagating movement from the lower hip region, supporting the back, and holding the shoulders upright when an individual wears garment 1. As shown, garment 1 is configured as a form-fitting garment and includes a form-fitting portion 2 configured to be worn by an individual's body and having a front section 4 and a back section 5 (FIG. 1B) and extends inferiorly from a shoulder section 6 of form-fitting portion 2 to leg sections 15 (alternatively referred to as lower appendage sections 15) of form-fitting portion 2. Garment 1 further includes an upper body section and a lower body section each having an interior surface area and an exterior surface area, where lower body section can be delineated from the upper body section by a waistline. For the purposes of this disclosure, the waistline may correspond with a transverse plane, which is a horizontal plane configured to divide an individual's body into an upper (superior) section and a lower (inferior) section. Furthermore, in embodiments, any portion of support structure 3 that wraps around hip section 7 can be considered to be below the waistline.

A support structure 3 includes an elastomeric band body and is affixed to the exterior surface area of the form-fitting portion 2. Support structure 3 is positioned on an upper body section and a lower body section of the form-fitting portion 2 and may act as a guidewire to modulate an individual's body at rest and during dynamic movement. As shown in the embodiment of FIGS. 1A, 1B, and 1C, support structure 3 is positioned on the upper and lower body sections of form-fitting portion 2. Structurally, support structure 3 wraps at least partially around first and second arm openings 9 of a shoulder section 6 of the front section 4, crisscrosses along the back section 5, and wraps around a hip section 7 of the front and back sections 4,5.

Support structure 3 further includes a posterior crisscross tightening structure 16 positioned on back section 5 that wraps around front portions of arm openings 9 (alternatively referred to as first and second upper appendage sections 9) on front section 4 and positioned in shoulder section 6. From the top of shoulder section 6, posterior crisscross tightening structure 16 extends inferiorly across an upper back section 10 (FIG. 1B) while also extending inferiorly along front section 4 around arm openings 9. Support structure 3 continues to extend inferiorly as lateral crisscross structures 17 across side sections 11 below arm openings 9 (FIG. 1C) to front hip section 7 and to a lower back section 12 (as lower tightening section 13), meeting/overlapping itself at a crotch portion 14 of form-fitting portion 2 (FIGS. 1A and 1B). Additionally, lower tightening section 13 wraps around lower appendage sections 15 of form-fitting portion 2 while being positioned through crotch portion 14. Additional band structures 22 also wrap around each of the lower appendage sections 15 and are positioned right below and adjacent the looped portions of support structure 3 wrapping around lower appendage sections 15.

In an embodiment (shown in FIGS. 1A, 1B, and 1C), support structure 3 comprises a pair of tensioning devices 18 each positioned along a respective one of the first upper appendage section 9 (one of arm openings 9) and the second upper appendage section 9 (the other of arm openings 9). The pair of tensioning devices are configured to perform at least one of increasing and decreasing tension applied to an individual's body when the garment 1 is worn by an individual.

In relation to the description of the support structure 3 above, in an embodiment the support structure 3 (shown in FIGS. 1A, 1B, and 1C) wraps around the first upper appendage section 9 and the first lower appendage section 15 in a first loop configuration. Support structure 3 additionally wraps around a second upper appendage section 9 and the second lower appendage section 15 in a second loop configuration. In relation to this embodiment, a balance of downward and upward compression forces are obtained between upper and lower appendages of an individual when an individual is wearing garment 1.

In an embodiment, the first loop configuration wraps around the first upper appendage section 9, extends across a back section 5 of the form-fitting portion 2, and wraps around a first diagonally opposing lower appendage section 15 of the first lower appendage section 15 and the second lower appendage section 15. Additionally, the second loop configuration wraps around the second upper appendage section 9, extends across the back section 5 of the form-fitting portion 2, and wraps around a second diagonally opposing lower appendage section 15 of the first lower appendage section 15 and the second lower appendage section 15. It is noted that the first and second loop configurations symmetrically cross a sagittal plane separating a left and right side of a garment wearer's body. In relation to this embodiment, a balance of downward and upward compression forces are obtained between upper and lower appendages of an individual when an individual is wearing the garment (leading to a balanced posture of an individual based on the forces applied to the individual's opposing appendages). As an example, the first loop configuration wraps around a front section (edge) of left arm opening 9, extends across the back section 5 of form-fitting section 2 (as two segments), and wraps around a front section of a right lower appendage section (right leg). Additionally, the second loop configuration wraps around a front section (edge) of right arm opening 9, extends across the back section 5 of form-fitting section 2 (as two segments), and wraps around a front section of a left lower appendage section (right leg). In this configuration, the first and second loop configurations are separate, contiguous structures. For the purposes of this disclosure, the connections of opposing appendages of an individual (legs and arms) may be referred to as a "cross pattern" that provides balanced tension forces, specifically, to an individual's shoulders and hips, which may lead to keeping the individual's shoulders down and back, keeps the individual's back straight, and keeps the individual's hips neutral/propagates the individual's hips (allowing for natural movement of multiple parts of the individual's body).

In an embodiment, the first loop configuration converges with the second loop configuration at a first side midsection point anatomically positioned between the first upper appendage section 9 and the first lower appendage section 15 and at a second side midsection point opposite the first side midsection point and anatomically positioned between the second upper appendage section 9 and the second lower appendage section 15. In relation to this embodiment, balanced upward compression forces are provided to hips of an individual wearing the garment 1, which may propagate movement in the lower hip region of an individual when an individual is wearing garment 1. Additionally, it is noted that the term "converges with", in relation to the first and second loop configurations, refers to the point where the support structure 3 (in the loop configuration) overlaps itself.

In an embodiment, the elastomeric band body of support structure 3 comprises two separate contiguous pieces of material. In relation to this embodiment, points of failure on the support structure 3 are minimized, which can increase the overall integrity of the garment 1.

In an embodiment, the elastomeric band body of support structure 3 is formed of an elastomeric fabric. In relation to this embodiment, a more seamless process of applying the support structure 3 to the form-fitting portion 2 can occur.

In an embodiment, support structure 3 at least partially wraps around a first upper appendage section (one of arm openings 9), a second upper appendage section (the other of arm openings 9), a first lower appendage section 15, and a second lower appendage section 15. In relation to this embodiment, anchor points are provided that assist in balancing out downward and upward compression forces when an individual is wearing the garment 1.

In embodiments relative to garment 1, support structure 3 includes a first elastomeric segment 8 extending medially from a first side of the shoulder section 6 of the upper body section of back section 5 (one of two segments 8,21 of posterior crisscross tightening structure 16). The first elastomeric segment 8 further extends through the crotch portion 14 of the lower body section. A second elastomeric segment 21 of support structure 3 extends medially from a second side of the shoulder section 6 of the upper body section of back section 5 (a second of two segments 8,21 of posterior crisscross tightening structure 16). The second elastomeric segment 21 further extends through the crotch portion 14 of the lower body section. In relation to this embodiment, an individual's shoulders can be pulled back and assisted into a proper/healthy postural shoulder pose when an individual is wearing the garment 1.

In an embodiment, the first elastomeric segment 8 further extends through the crotch portion 14, wraps around a first front side of hip section 7 of the lower body section, extends across the second elastomeric segment 21 at a first side section 11 (one of two lateral crisscross structures 17), and extends across the upper body section to the first side (same side of where the first elastomeric segment 8 started) of the shoulder section 6. Additionally, the second elastomeric segment 21 further extends through the crotch portion 14, wraps around a second front side of hip section 7 of the lower body section, extends across the first elastomeric segment 8 at a second side section 11 (one of two lateral crisscross structures 17), and extends across the upper body section to the second side (same side of where the second elastomeric segment 21 began) of the shoulder section 6. In relation to this embodiment, balanced upward compression forces are provided to hips of an individual wearing the garment 1, which may propagate movement in the lower hip region of an individual wearing the garment 1.

In an embodiment, the support structure 3 includes a first elastomeric segment 8 wrapping around a front portion of a first upper appendage section 9 (FIG. 1A), extending across an upper back section 5 (one of two segments 8,21 of posterior crisscross tightening structure 16), and extending medially toward a midline of the garment 1. Additionally, the support structure includes a second elastomeric segment 21 wrapping around a front portion of a second upper appendage section 9 (FIG. 1A), extending across the upper back section 5 (a second of two segments 8,21 of posterior crisscross tightening structure 16), and extending medially toward the midline of the garment 1. In relation to this embodiment, balanced upward compression forces are provided to hips of an individual wearing the garment 1, which may propagate movement in the lower hip region of an individual.

In an embodiment, the first elastomeric segment 8 and the second elastomeric segment 21 cross one another at the crotch portion 14, where the first elastomeric segment 8 and the second elastomeric segment 21 are absent an attachment structure at the crotch portion 14, the attachment structure configured to directly connect support structure 3 to form-fitting portion 2. In relation to this embodiment, the spine is able to nutate with the hips and allows the spine and shoulders to be in opposition with the hips when an individual is wearing garment 1. As an example, the first elastomeric segment 8 and the second elastomeric segment 21 are absent stitching at the crotch portion 14.

It is noted that short-legged garment 1 may be configured to assist an individual with extended sitting, working out, and later stage pregnancy support. Specifically, short-legged garment 1, via support structure 3, may provide support to an individual's back as well as properly balance out and support the back via lateral crisscross structures 17 across side sections 11 that may provide balanced downward compression forces to posterior crisscross tightening structure 16/shoulder section 6 and balanced upward compression forces to lower tightening section 13/hip section 7. This may directly assist these individuals with muscle support that may make the extended sitting, working out, and later state pregnancy support easier to perform.

In order to provide assistance in propagating movement from an individual's lower hip region, the lateral crisscross structures 17 across side sections 11 may provide balanced upward compression forces to lower tightening section 13/hip section 7 (when worn by an individual), thus propagating movement in the lower hip region. More specifically, lower tightening section 13 may assist an individual in moving the individual's pelvis from a neutral position to either of an anterior pelvic tilt and a posterior pelvic tilt.

In order to provide support to an individual's back, the lateral crisscross structures 17 across side sections 11 may provide balanced downward compression forces to posterior crisscross tightening structure 16/shoulder section 6 while also providing balanced upward compression forces to lower tightening section 13/hip section 7 in order to also properly balance out and support the back. Anatomically speaking, the upper trapezius and levator scapula are both retracted by posterior crisscross tightening structure 16, while the individual's gluteus maximus muscles are protracted and the individual's rectus abdominis muscles are retracted by lower tightening section 13.

In addition to supporting an individual's back, the balanced downward compression forces applied to posterior crisscross tightening structure 16/shoulder section 6 by the lateral crisscross structures 17 may also provide assistance in holding an individual's shoulders upright. Again, the upper trapezius and levator scapula may both be retracted by posterior crisscross tightening structure 16, thus assisting in holding an individual's shoulders upright.

Figure 2C:
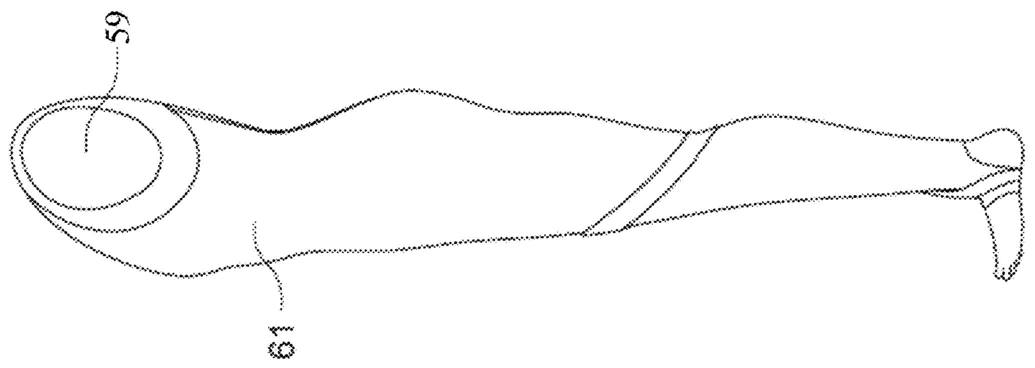
FIG. 2C displays a side view of a long-legged garment for supporting posture of an individual in accordance with embodiments.
Figure 2B:
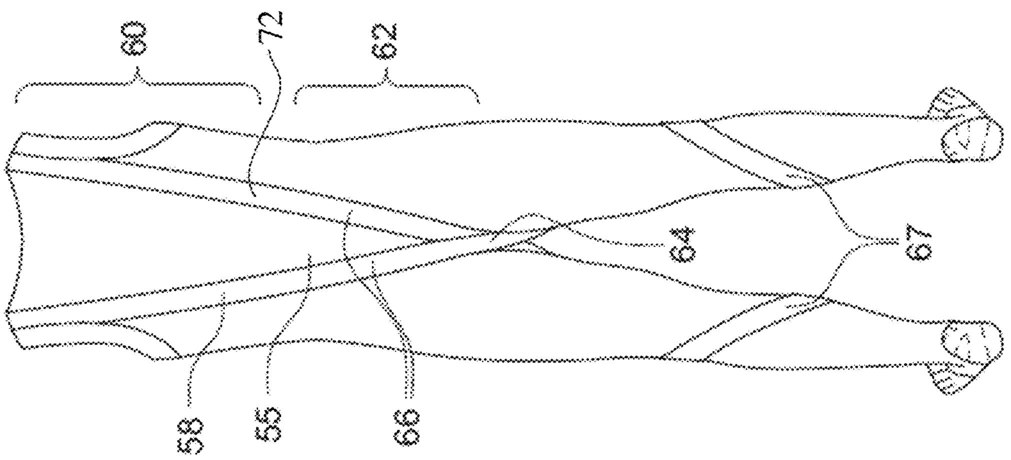
FIG. 2B displays a rear view of a long-legged garment for supporting posture of an individual in accordance with embodiments.
Figure 2A:
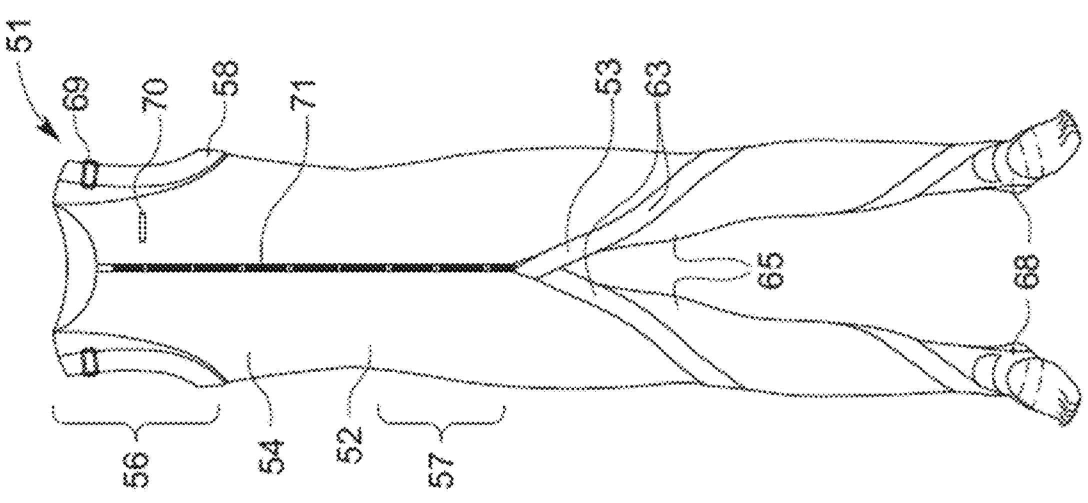
FIG. 2A displays a front view of a long-legged garment for supporting posture of an individual in accordance with embodiments.

FIG. 2A displays a front view of a long-legged garment 51 for promoting posture in accordance with embodiments. Garment 51 may be configured to assist an individual in lifting the mid-arches of the feet, winding the hips for internal rotation, holding the back upright, and keeping the shoulders back when an individual wears garment 51. As shown, garment 51 is configured as a form-fitting garment and includes a form-fitting portion 52 configured to be worn by an individual's body and having a front section 54 and a back section 55 (FIG. 3B) and extends inferiorly from a shoulder section 56 of form-fitting portion 52 to leg sections 65 (alternatively referred to as lower appendage sections 65) of form-fitting portion 52. Garment 51 further includes an upper body section and a lower body section each having an interior surface area and an exterior surface area, where lower body section can be delineated from the upper body section by a waistline. For the purposes of this disclosure, the waistline may correspond with a transverse plane, which is a horizontal plane configured to divide an individual's body into an upper (superior) section and a lower (inferior) section. Furthermore, any portion of support structure 53 that wraps around hip section 57 can be considered to be below the waistline.

A support structure 53 includes an elastomeric band body and is affixed to the exterior surface area of the form-fitting portion 52. Support structure 53 is positioned on an upper body section and a lower body section of the form-fitting portion 52 and may act as a guidewire to modulate an individual's body at rest and during dynamic movement. As shown in the embodiment of FIGS. 2A, 2B, and 2C, support structure 53 is positioned on the upper and lower body sections of form-fitting portion 52. Structurally, support structure 53 wraps at least partially around first and second arm openings of a shoulder section of the front section 54, extends inferiorly along the back section 55, and wraps around a hip section 57 of the front and back sections 54,55.

Support structure 53 further includes a posterior medially converging structure 66 (alternatively referred to as an upper tightening section) positioned on back section 55 that wraps around front portions of arm openings 59 positioned in shoulder section 56. From the top of shoulder section 56, posterior medially converging structure 66 extends inferiorly along an upper back section 60 and lower back section 62 to a lower rear crotch portion 64 (FIG. 2B), while also extending inferiorly along front section 54 around arm openings 59 (FIG. 2C). Support structure 53 continues to extend (as lower tightening section 63) through crotch portion 64 (FIG. 3A) and curl around (as inferiorly extending structures 67) leg sections 65 of form-fitting portion 52. The inferiorly extending structures 67 may terminate at a pair of foot sections 68 that extend down to and circumnavigate the feet (as shown, stirrup portions) of an individual when an individual is wearing garment 51. It is noted that foot sections 68 may assist an individual in lifting the mid-arches of the feet, allowing more weight to be placed on the balls of an individual's feet (as well as providing arch support)

Figure 3B:
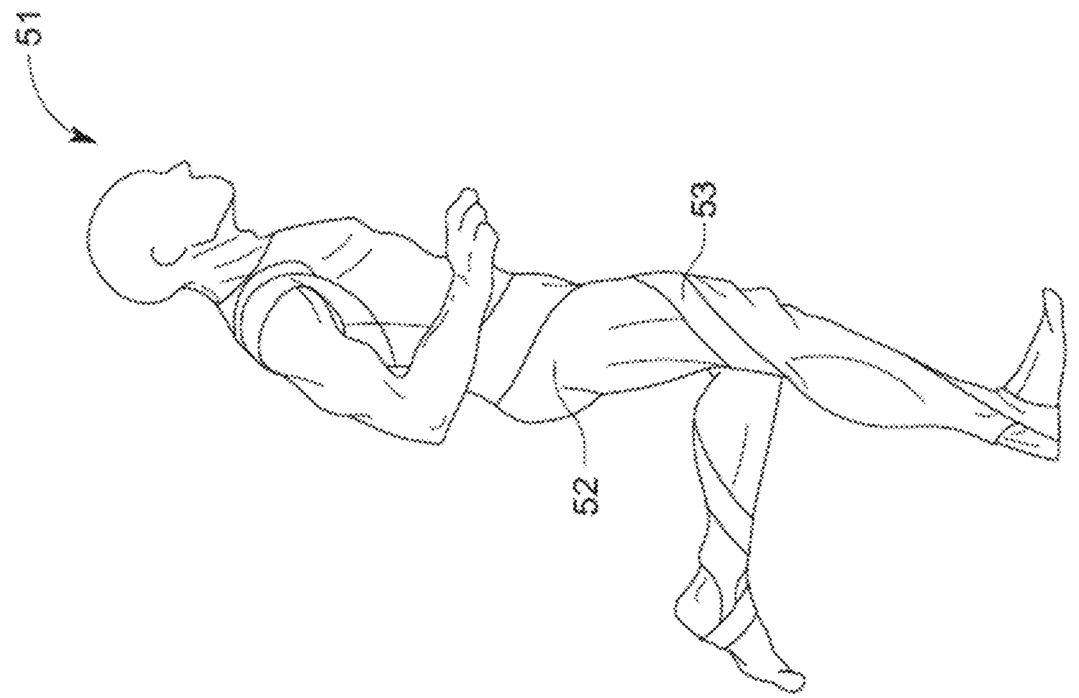
FIG. 3B displays a side view of an individual wearing a posture supporting long-legged garment in accordance with embodiments.
Figure 3A:
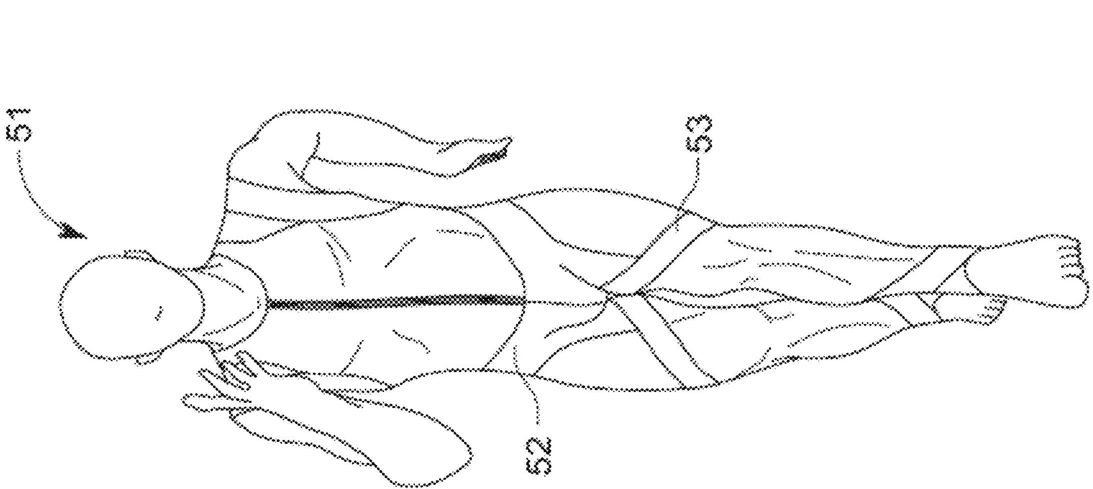
FIG. 3A displays a front view of an individual wearing a posture supporting long-legged garment in accordance with embodiments.

FIGS. 3A and 3B display front and side views of an individual wearing a long-legged garment 51 in accordance with embodiments. As shown, the individual is shown in different positions while running. When running, long-legged garment 51 may provide assistance in lifting an individual's mid-arches of their feet (provides arch support for the individual, as well as allowing more weight to be placed on the balls of an individual's feet), provide assistance in winding the hips of an individual (helps reduce the likelihood of compensation injuries and muscle cramps), provide assistance in holding the back of an individual upright (helps reduce the likelihood of back injuries), and provide assistance in keeping an individual's shoulders back (helps reduce the likelihood of back injuries and neck injuries) when an individual is wearing garment 51. In addition, long-legged garment 52 may provide more efficient glute activation (compared to other sportswear), may provide increased back stabilization, and may promote/engage hip movement. This may allow an individual to have a more effective and safer running experience. It is further noted that balanced upward and downward tension forces are applied by the configuration of support structure 53, leading to portions of an individual's body being more easily positioned in a beneficial postural pose when the individual's body is either at rest or in motion.

In an embodiment, support structure 53 extends from a shoulder section 56 of the form-fitting portion 52 to a pair of foot sections 68 of the form-fitting portion 52. In relation to this embodiment, a majority of an individual's body can be modulated at one time when an individual is wearing the garment 51.

In an embodiment, support structure 53 at least partially wraps around a first upper appendage section (one of arm openings 59), a second upper appendage section (the other of arm openings 59), a first lower appendage section 65, and a second lower appendage section 65. In relation to this embodiment, anchor points (at the appendage sections) are provided that assist in balancing out downward and upward compression forces when an individual is wearing the garment 51.

In an embodiment, support structure 53 includes a pair of tensioning devices 69 each positioned along a respective one of the first upper appendage section 59 and the second upper appendage section 59, where the pair of tensioning devices 69 are configured to perform at least one of increasing and decreasing tension applied to an individual's body when the garment 51 is worn by an individual. In relation to this embodiment, compression forces on an individual's body can be changed which can lead to additional comfort for an individual when an individual is wearing the garment 51.

In embodiments relative to garment 51, support structure 53 includes a first elastomeric segment 58 extending medially from a first side of the shoulder section 56 of the upper body section of back section 55 (one of two segments 58,72 of posterior medially converging structure 66). The first elastomeric segment 58 further extends through the crotch portion 64 of the lower body section. A second elastomeric segment 72 of support structure 53 extends medially from a second side of the shoulder section 56 of the upper body section of back section 55 (a second of two segments 58,72 of posterior medially converging structure 66). The second elastomeric segment 72 further extends through the crotch portion 64 of the lower body section. In relation to this embodiment, an individual's shoulders can be pulled back and assisted into a proper/healthy postural shoulder pose when an individual is wearing the garment 51.

In an embodiment, first elastomeric segment 58 further extends in a spiral configuration along a first lower appendage section 65 of the form-fitting portion 52 and the second elastomeric segment 72 further extends in a spiral configuration along a second lower appendage section 65 of the form-fitting portion 52. As shown, the spiral configuration is an internally rotating spiral configuration, which may lead to an individual's hips being rotated internally. Additionally, the first elastomeric segment 58 and the second elastomeric segment 72 are configured to internally rotate hips of an individual, to hold the individual's back upright, and to pull the individual's shoulders back when the individual is wearing the garment 51. It is noted that internal rotation of the individual's hips switches on the individual's glutes, keeps the back tall and extended, and allows for natural movement from the individual's body when the individual is wearing garment 51. It is further noted that the term "switches", in relation to muscles in an individual's body (such as the glutes), refers to one more muscles being turned on neurologically (activates the muscles).

In an embodiment, each of the first elastomeric segment 58 and the second elastomeric segment 72 terminate at a respective one of a first loop end and a second loop end located at foot sections 68, where each of the first loop end and the second loop end are configured to wrap around a respective one of a first foot and a second foot of an individual to lift mid-arches of the first foot and second foot when an individual is wearing the garment 51.

In an embodiment, first elastomeric segment 58 and the second elastomeric segment 72 cross one another at a convergence point at the crotch portion 64 and extend laterally away from the convergence point along respective first and second lower appendage sections 65. Additionally, the first elastomeric segment 58 and the second elastomeric segment 72 are configured to internally rotate hips of an individual, to hold the individual's back upright, and to pull the individual's shoulders back when the individual is wearing the garment 51.

In an embodiment, the elastomeric band body of support structure 53 is formed of an elastomeric fabric. In relation to this embodiment, a more seamless process of applying the support structure 53 to the form-fitting portion 52 can occur.

In an embodiment, the first elastomeric segment 58 and the second elastomeric segment 72 cross one another at the crotch portion 64, where the first elastomeric segment 58 and the second elastomeric segment 72 are absent an attachment structure at the crotch portion 64, the attachment structure configured to directly connect support structure 53 to form-fitting portion 52. In relation to this embodiment, the spine is able to nutate with the hips and allows the spine and shoulders to be in opposition with the hips when an individual is wearing garment 51. As an example, the first elastomeric segment 58 and the second elastomeric segment 72 are absent stitching at the crotch portion 64.

In order to provide assistance in lifting an individual's mid-arches of their feet, the inferiorly extending structures 67 extending along leg sections 65 may provide balanced upward compression forces to the pair of stirrup portions 68 encircling the feet of the individual. Anatomically speaking, the mid-arches may be retracted by lower tightening section 63, which may provide arch support for the individual.

In order to provide assistance in winding the hips of an individual, balanced upward compression forces provided by the medially converging structure 66 and the inferiorly extending structures 67 may pull the lower hips posteriorly and the upper hips anteriorly so that the individual's hips are properly wound. Anatomically speaking, the individual's gluteus maximus muscles are protracted and the individual's rectus abdominis muscles are retracted by posterior medially converging structure 66 and lower tightening section 63, which may help reduce the likelihood of compensation injuries and muscle cramps for an individual.

In order to provide assistance in holding the back of an individual upright, the medially converging structure 66 may provide downward compression forces to posterior medially converging structure 66/shoulder section 56 while also providing upward compression force to hip section 57 in order to properly hold the back upright. Anatomically speaking, the upper trapezius and levator scapula are both retracted by posterior medially converging structure 66, while the individual's gluteus maximus muscles are protracted and the individual's rectus abdominis muscles are retracted by lower tightening section 63, which may help reduce the likelihood of back injuries for an individual.

In order to provide assistance in keeping an individual's shoulders back, the medially converging structure 66 may provide downward compression forces to posterior medially converging structure 66/shoulder section 56 in order to properly keep the shoulders back. Again, the upper trapezius and levator scapula are both retracted by posterior medially converging structure 66, which may help reduce the likelihood of back injuries and neck injuries for an individual.

In an embodiment, short-legged garment 1 may include a pair of tensioning devices 18 with each tensioning device 18 affixed to opposite front portions of support structure 3 (shoulder section 6). In an additional embodiment, long-legged garment 51 may include a pair of tensioning devices 69 with each tensioning device 69 affixed to opposite front portions of support structure 53 (shoulder section 56). In an embodiment, each tensioning device 18,69 may comprise a clip portion and a receiving portion. The clip portion may be affixed to one end of support structure 3/support structure 53 while the receiving portion may be affixed to another end of support structure 3/support structure 53; the clip portions and receiving portions affix at the front shoulders of an individual. Clips 18,69 may assist an individual in making it easier to put on short-legged garment 1/long-legged garment 51 by reducing the compression force placed on an individual's body by posterior crisscross tightening structure 16/posterior medially converging structure 66. In additional embodiments, clips 18,69 may additionally provide an individual the option to increase or decrease compression forces of support structure 3,53 on an individual's body; for example, clips 18, 69 may be of a configuration similar to a buckle and holes (or a similar configuration that provides a potential segmented increase or decrease in tension). In additional embodiments, leg garment 101, bra garment 151, and/or underwear garment 201 may include a pair of tensioning devices (not shown) that may function similarly as described above.

In embodiments, the tensioning devices 18,69 may be clips configured to be affixed to bands of support structures 3,53.

Figure 4C:
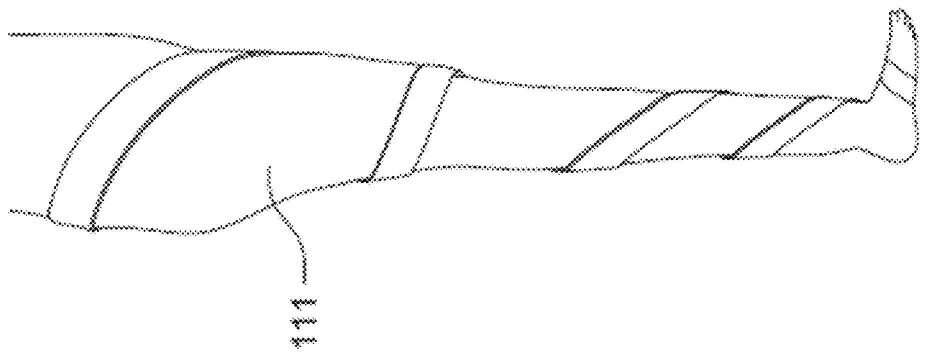
FIG. 4C displays a side view of a leg garment for supporting posture of an individual in accordance with embodiments.
Figure 4B:
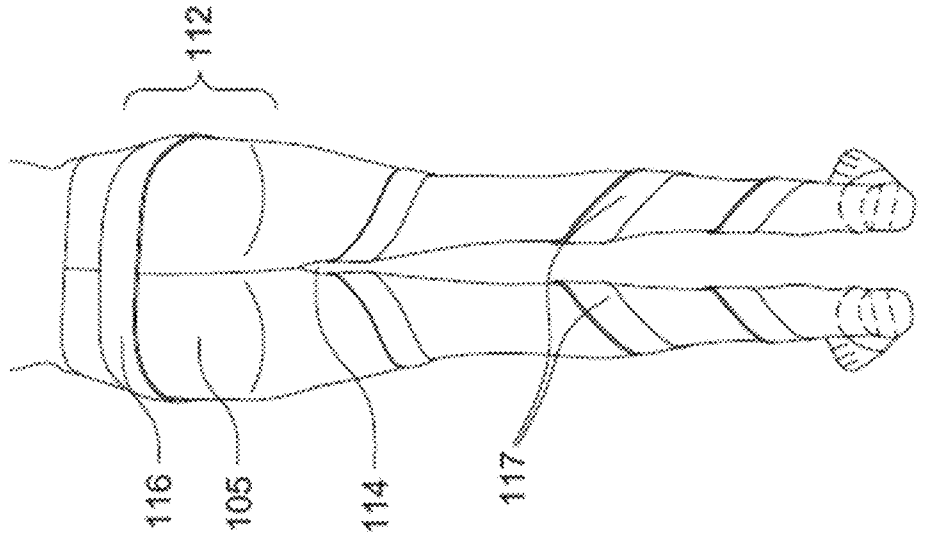
FIG. 4B displays a rear view of a leg garment for supporting posture of an individual in accordance with embodiments.
Figure 4A:
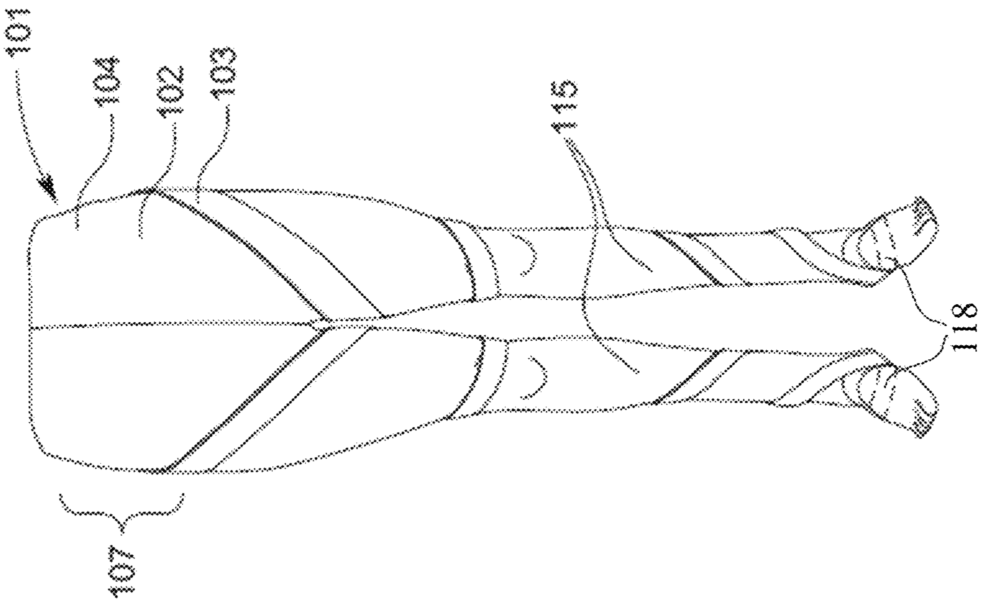
FIG. 4A displays a front view of a leg garment for supporting posture of an individual in accordance with embodiments.

FIG. 4A displays a front view of a leg garment 101 for promoting posture in accordance with embodiments. Garment 101 may be configured to assist an individual in winding the hips for internal rotation and supporting the lower back. Garment 101 includes a form-fitting portion 102 having a front section 104 and a back section 105 (FIG. 4B) that extends from a hip section 107 of form-fitting portion 102 to leg sections 115 of form-fitting portion 102. A support structure 103 integral with the form-fitting portion 102 wraps around an upper portion of rear section 112, extends downward across side sections 111, and winds around leg sections 115 that overlaps front and back sections 104,105. Support structure 103 includes a rear structure 116 that extends laterally across an upper portion of rear section 112 and then downward along side sections 111 (FIG. 4C). Support structure 103 may continue to extend through crotch portion 114 (FIG. 4A) and curl around (as inferiorly extending structures 117) leg sections 115 of form-fitting portion 102. The inferiorly extending structures 117 may terminate at a pair of stirrup portions 118 (similar to stirrup portions 68 of long-legged garment 51) that extend down to and circumnavigate the feet of an individual.

In an embodiment, the elastomeric band body of support structure 103 comprises a single contiguous piece of material. In relation to this embodiment, points of failure on the support structure 103 are minimized, which can increase the overall integrity of the garment 101.

In an embodiment, the elastomeric band body of support structure 103 is formed of an elastomeric fabric. In relation to this embodiment, a more seamless process of applying the support structure 103 to the form-fitting portion 102 can occur.

In order to provide assistance in winding the hips of an individual, balanced upward compression forces provided by the rear structure 116 and the inferiorly extending structures 117 may pull the lower hips posteriorly and the upper hips anteriorly so that the individual's hips are properly wound when an individual is wearing garment 101. Anatomically speaking, the individual's gluteus maximus muscles are protracted and the individual's rectus abdominis muscles are retracted by rear structure 116 and interiorly extending structures 117, which may help reduce the likelihood of compensation injuries and muscle cramps. In addition, the pelvis may be placed in a neutral position or may be encouraged to maintain equilibrium and a neutral positioning.

In order to provide assistance in supporting an individual's lower back, the balanced upward compression forces provided by the rear structure 116 and the inferiorly extending structures 117 may pull the lower back forward. Anatomically speaking, portions of the lower spine of an individual wearing garment 101 may be pulled forward, which may reduce any exaggeration in the lumbar curve (due to bad posture) so that the spine may sit straighter.

Figure 5B:
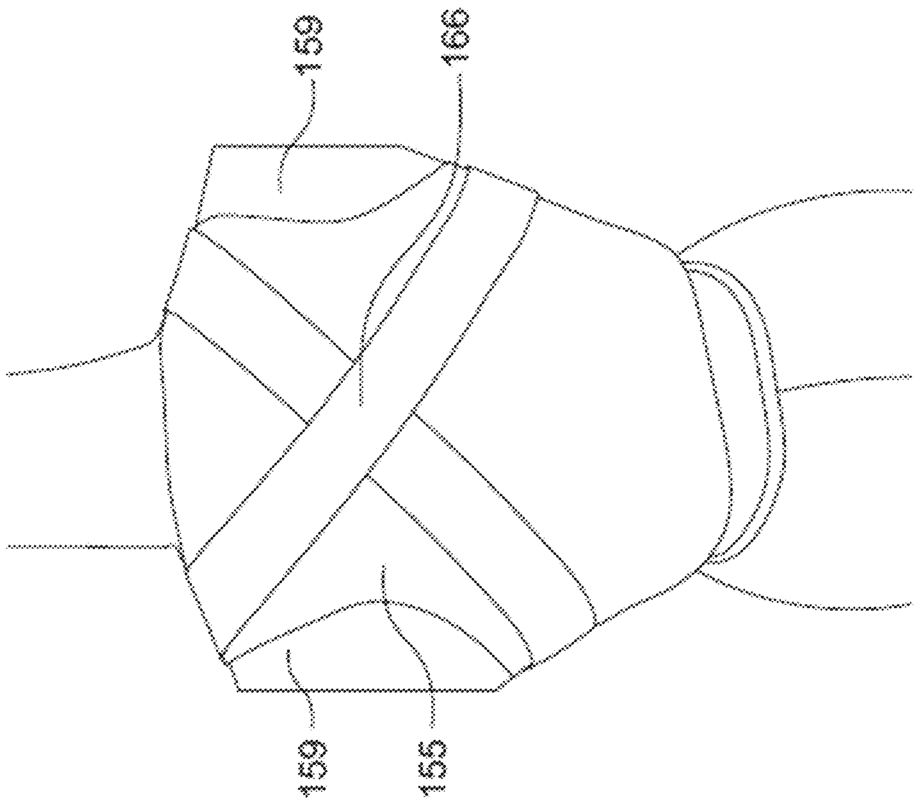
FIG. 5B displays a rear view of a bra garment for supporting posture of an individual in accordance with embodiments.
Figure 5A:
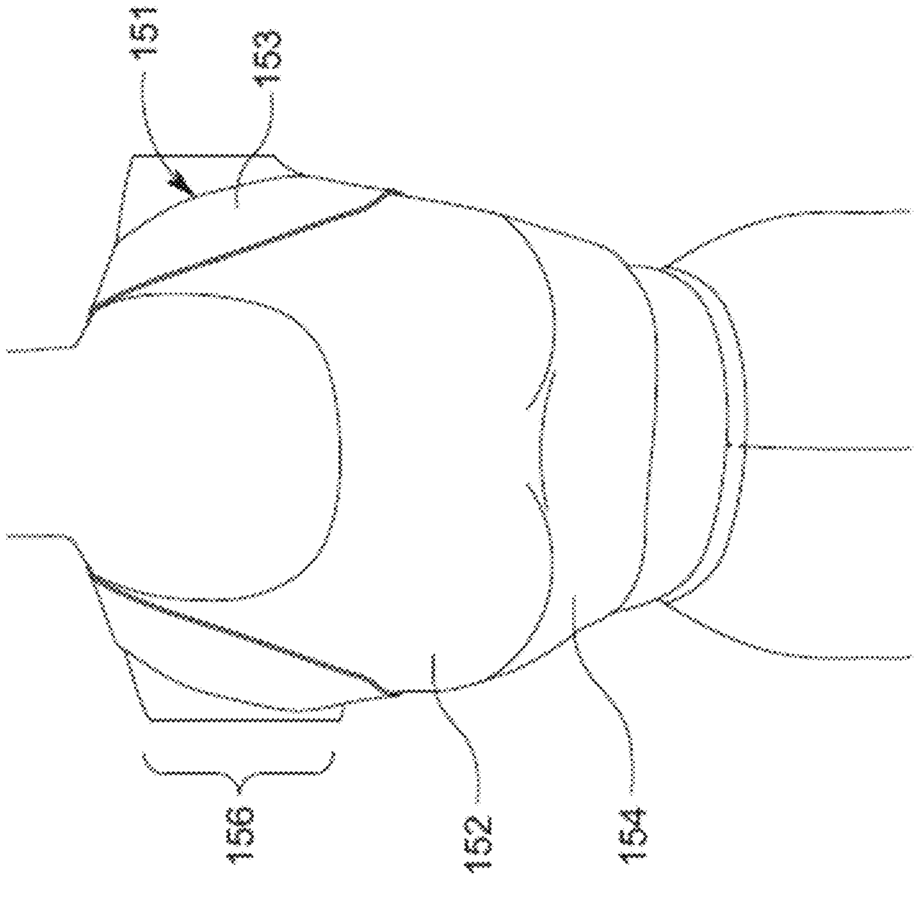
FIG. 5A displays a front view of a bra garment for supporting posture of an individual in accordance with embodiments.

FIG. 5A displays a front view of a bra garment 151 for promoting posture in accordance with embodiments. Garment 151 may be configured to assist an individual in holding their shoulders upright. Garment 151 includes a form-fitting portion 152 having a front section 154 and a back section 155 (FIG. 5B) that extends from a shoulder section 156 of form-fitting portion 152 and terminates at roughly an individual's stomach area (or below armpits of the individual). A support structure 153 integral with the form-fitting portion 152 wraps around shoulder section 156 of the front section 154 and crisscrosses across back section 155. Support structure 3 wraps around (above and below) front portions of arm openings 159 positioned within shoulder section 156. From shoulder section 156, support structure 153 extends posteriorly as a posterior crisscross tightening structure 166 across back section 155 (FIG. 7B).

In order to provide assistance in holding an individual's shoulders upright, balanced anterior and posterior compression forces may be applied to shoulder section 156 via the front of support structure 153 as well as the posterior crisscross tightening structures 166. Anatomically speaking, the upper trapezius and levator scapula may both be retracted by support structure 153, thus assisting in holding an individual's shoulders upright.

In an embodiment, the elastomeric band body of support structure 153 comprises a single contiguous piece of material. In relation to this embodiment, points of failure on the support structure 153 are minimized, which can increase the overall integrity of the garment 151.

In an embodiment, the elastomeric band body of support structure 153 is formed of an elastomeric fabric. In relation to this embodiment, a more seamless process of applying the support structure 153 to the form-fitting portion 152 can occur.

Figure 6C:
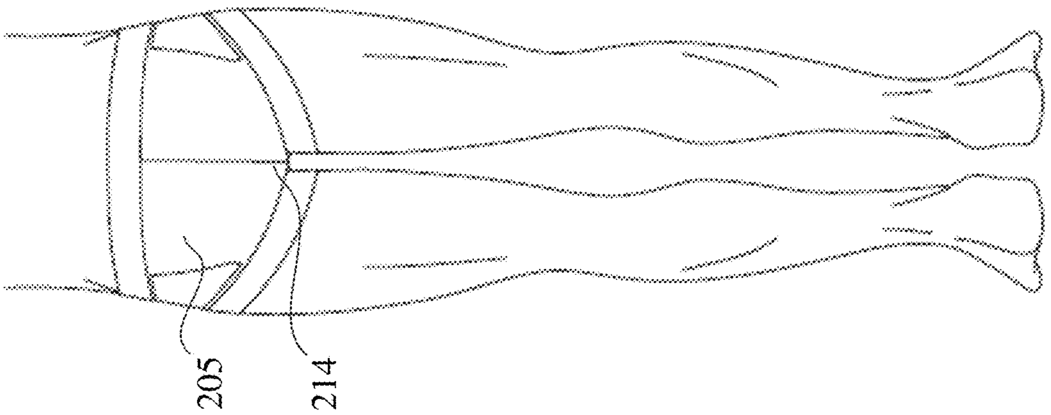
FIG. 6C displays a rear view of an underwear garment for supporting posture of an individual in accordance with embodiments.
Figure 6B:
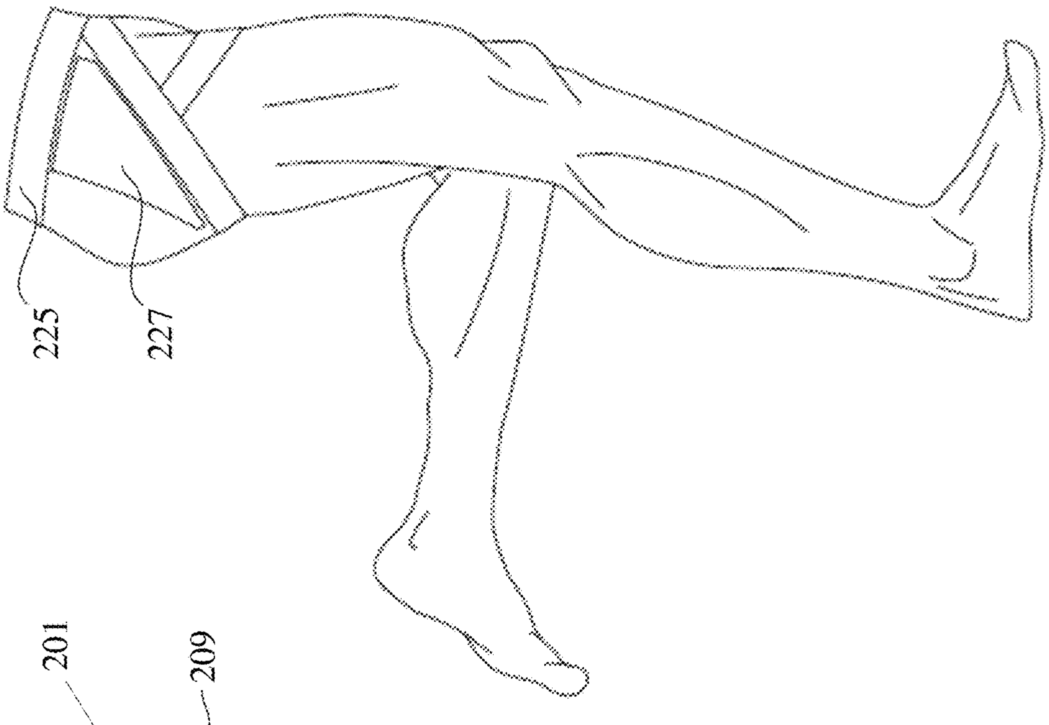
FIG. 6B displays a side view of an underwear garment for supporting posture of an individual in accordance with embodiments.
Figure 6A:
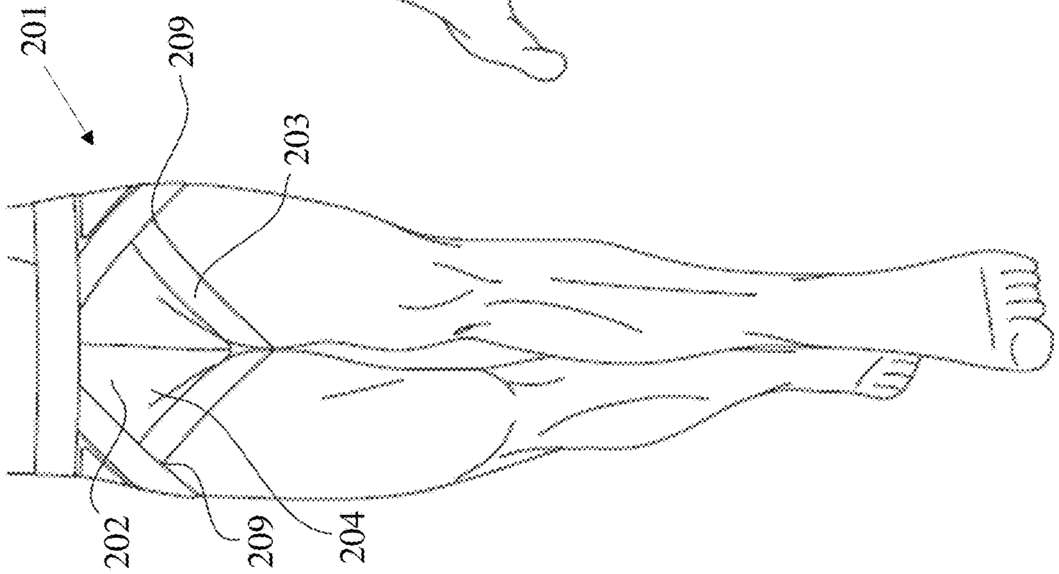
FIG. 6A displays a front view of an underwear garment for supporting posture of an individual in accordance with embodiments.

FIG. 6A displays a front view of an underwear garment 201 for supporting posture of an individual in accordance with embodiments. Garment 201 may be configured to assist an individual in holding the individual's pelvis upright and in a neutral position when an individual is wearing the garment 201. The balancing front and rear tensioning forces of garment 201 are configured to hold an individual's pelvis upright and in a neutral position. As shown, garment 201 is configured as a form-fitting garment and includes a form-fitting portion 202 configured to be worn by an individual's body and having a front section 204 and a back section 205 (FIG. 6C). Garment 201 extends inferiorly from a waistband 225 to lower portions of an individual's legs and includes an interior surface area and an exterior surface area.

A support structure 203 includes an elastomeric band body and is affixed to the exterior surface area of the form-fitting portion 202. Support structure 203 may act as a guidewire to modulate an individual's body at rest and during dynamic movement. As shown in the embodiment of FIGS. 6A, 6B, and 6C, structurally, support structure 203 extends laterally and inferiorly from separate sides of waistband 225, wraps around first and second leg openings 209 of garment 201 (across side sections 227, see FIG. 6B) while also wrapping around a lower glute region of back section 205 (FIG. 6B), medially converges at a crotch region 214, and continues wrapping around front section 204 until support structure 203 converges with itself.

In relation to support structure 203, the portions of support structure 203 positioned along a lower glute region of form-fitting portion 202 is configured as anchor segments that join waistband 225 at a pelvic region of form-fitting portion 202 (in front of an individual's pelvis). This configuration may be configured to isolate the pelvis via front and rear tensioning forces, allowing for extension of an individual's hips without an individual involving their lower back when an individual is wearing garment 202.

Figure 7C:
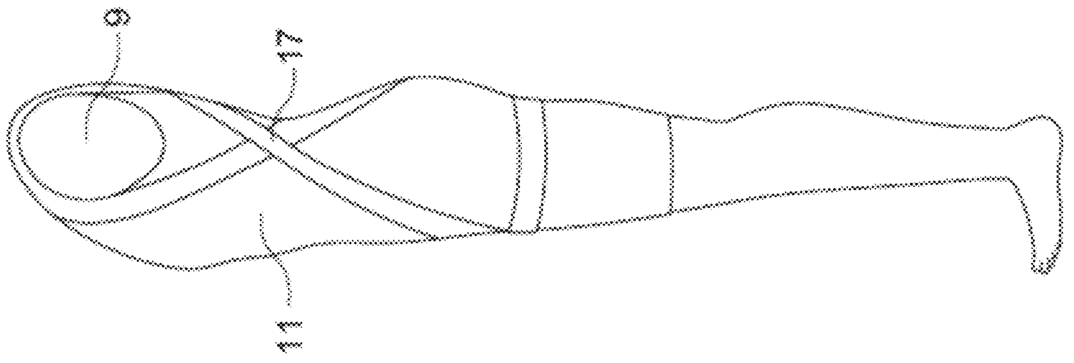
FIG. 7C displays a side view of an alternative short-legged garment for supporting posture of an individual in accordance with embodiments.
Figure 7B:
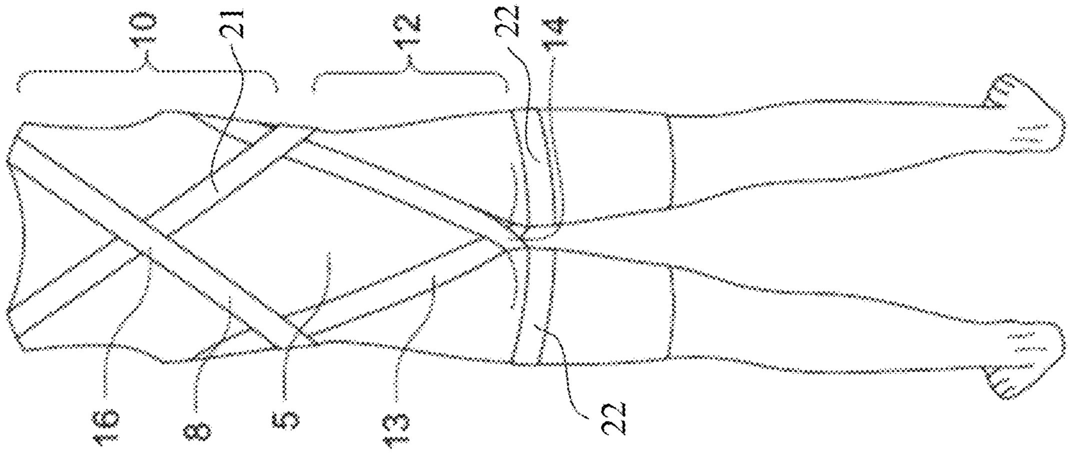
FIG. 7B displays a rear view of an alternative short-legged garment for supporting posture of an individual in accordance with embodiments.
Figure 7A:
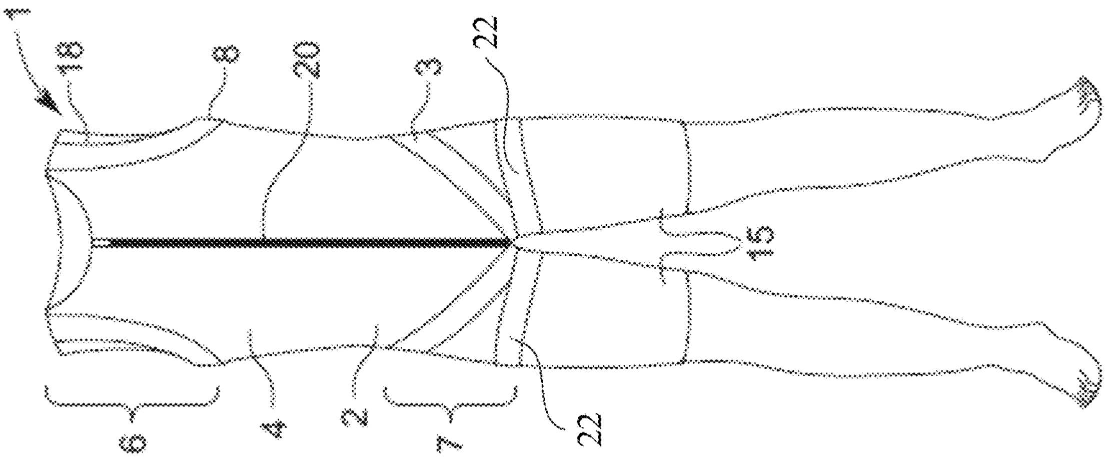
FIG. 7A displays a front view of an alternative short-legged garment for supporting posture of an individual in accordance with embodiments.

FIGS. 7A, 7B, and 7C display front, rear, and side views of an alternative short-legged garment 1 for supporting posture of an individual in accordance with embodiments.

As shown, the embodiment presented may be similar to the embodiment found in FIGS. 1A, 1B, and 1C, but may exclude a pair of tensioning devices 18 and logo 19.

Figure 8A:
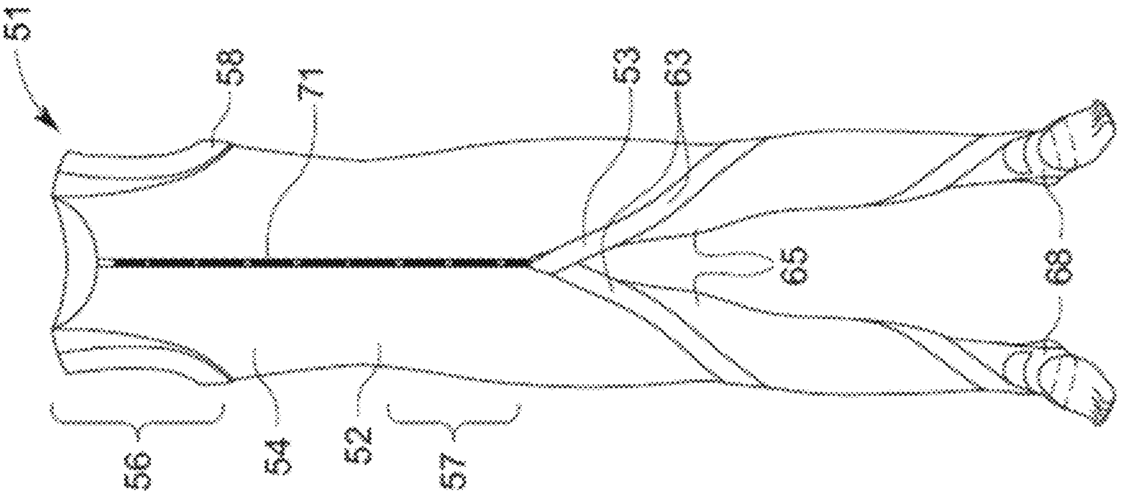
FIG. 8A displays a front view of an alternative long-legged garment for supporting posture of an individual in accordance with embodiments.
Figure 8B:
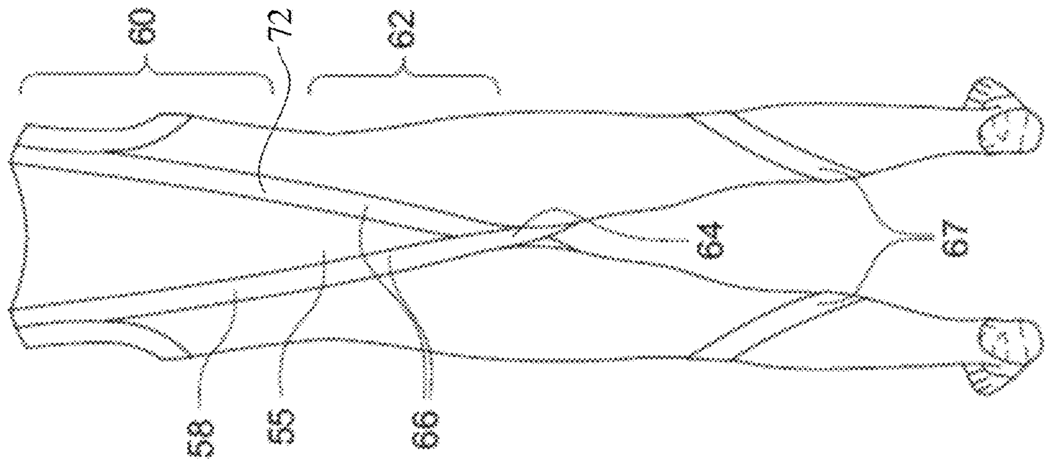
FIG. 8B displays a rear view of an alternative long-legged garment for supporting posture of an individual in accordance with embodiments.
Figure 8C:
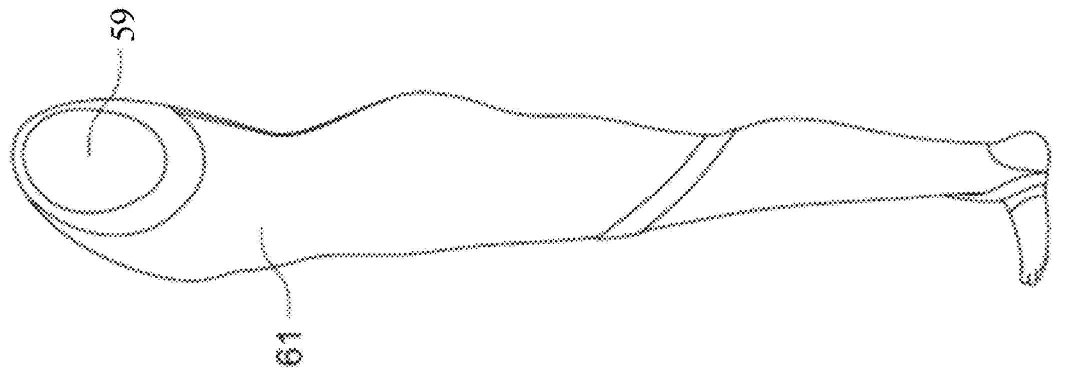
FIG. 8C displays a side view of an alternative long-legged garment for supporting posture of an individual in accordance with embodiments.

FIGS. 8A, 8B, and 8C display front, rear, and side views of an alternative long-legged garment 51 for supporting posture of an individual in accordance with embodiments. As shown, the embodiment presented may be similar to the embodiment found in FIGS. 2A, 2B, and 2C, but may exclude a pair of tensioning devices 69 and logo 70.

Figure 9:
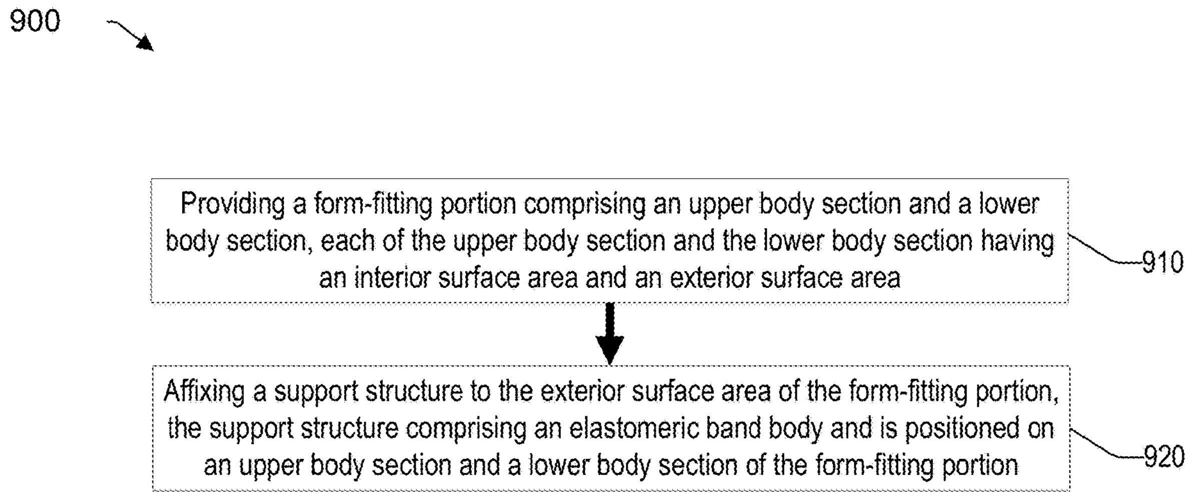
FIG. 9 is a flowchart for a method of forming a garment for supporting posture of an individual in accordance with embodiments.

With the foregoing overview of the example garment 1,51,101,151,201, it may be helpful to consider a high-level discussion of an example process. To that end, FIG. 9 presents a flowchart 900 for a method of forming a garment for supporting posture of an individual in accordance with embodiments.

Flowchart 900 is illustrated as a process in logical flowchart format. The order in which the operations are described is not intended to be construed as a limitation. For discussion purposes, the method of forming a garment for supporting posture of an individual is described with reference to the configurations of garments 1,51 of FIGS. 1A,1B, 1C and FIGS. 2A,2B,2C. Additionally, it can be understood by one skilled in the art to utilize and apply similar process steps in the method for supporting posture of an individual to any of the other disclosed garments.

At block 910, a form-fitting portion 2,52 is provided. Form-fitting portion 2,52 includes an upper body section and a lower body section, where each of the upper body section and the lower body section have an interior surface area and an exterior surface area.

At block 920, a support structure 3,53 is affixed to the exterior surface area of the form-fitting portion 2,52. Support structure 3,53 includes an elastomeric band body and is positioned on an upper body section and a lower body section of the form-fitting portion 2,52. The method is advantageous in that the support structure 3,53 may act as a guidewire to modulate an individual's body at rest and during dynamic movement when an individual is wearing the garment 1,51.

In embodiments, the affixing further includes affixing a first loop configuration of the support structure 3,53 around a first upper appendage section 9,59 of the form-fitting portion 2,52, across a back section 5,55 of the form-fitting portion 2,52, and around a first diagonally opposing lower appendage section 15,65 of the form fitting portion 2,52. The affixing additionally includes affixing a second loop configuration around a second upper appendage section 9,59 of the form-fitting portion 2,52, across the back section 5,55 of the form-fitting portion 2,52, and around a second diagonally opposing lower appendage section 15,65 of the form-fitting portion 2,52. In relation to this embodiment, a balance of downward and upward compression forces are obtained between upper and lower appendages of an individual when an individual is wearing the garment 1,51.

In embodiments, the affixing further includes affixing a first elastomeric segment 8,58 extending medially from a first side of a shoulder section 6,56 of the upper body section, through a crotch portion 14,64 of the lower body section, and along a first lower appendage section 15,65 of the lower body section in a spiral configuration. The affixing additionally includes affixing a second elastomeric segment 21,72 extending medially from a second side of the shoulder section 6,56 of the upper body section, through the crotch portion 14,64 of the lower body section, and along a second lower appendage section 15,65 of the lower body section in a spiral configuration. In relation to this embodiment, the first elastomeric segment 8,58 and the second elastomeric segment 21,72 are configured to internally rotate hips of an individual, to hold the individual's back upright, and to pull the individual's shoulders back when the individual is wearing the garment 1,51.

In embodiments, additional limitations of the method of FIG. 9 may include details relative to the structures of form-fitting portions 2,52 and/or support structures 3,53.

In embodiments, additional methods include a "providing" and an "affixing" in relation to garments 101,151,201. The "providing" may include providing a form fitting portion relative to the structure of form-fitting portions 102, 152,202 of garments 101,151,201. The "affixing" may include affixing a support structure to the exterior surface area of the form-fitting portion relative to the structure of support structures 103,153,203 of garments 101,151,201. In additional embodiments, additional limitations of the method of FIG. 9 may include details relative to the structures of form-fitting portions 102,152,202 and/or support structures 103,153,203.

It is noted that short-legged garment 1, long-legged garment 51, leg garment 101, bra garment 151, and underwear garment 201 may be configured to facilitate improved alignment and posture to an individual's body. Improved alignment and posture may allow for an individual's body movements to become more optimized, which may in turn reduce input to the nervous system (and allowing the nervous system to use its resources for more demanding needs). Further, support structures 3,53,103,153,203 of short-legged garment 1, long-legged garment 51, leg garment 101, bra garment 151, and underwear garment 201 may act as "guidewires" in movement for an individual's body when garments 1,51,101,151,201 are worn, supplementing tensegrity to the body of the individual. Additionally, the support structures 3,53,103,153,203 may provide assistance with repatterning and/or restructuring the physical movements of an individual utilizing any of garments 1,51,101,151,201 which may increase the overall health of the individual/individual's body.

It is noted that the more (any of) garments 1,51,101,151, 201 align an individual's body, the easier it may be to provide new neurological input to the individual's body. Additional compression of an individual's body may provide additional muscle dampening, which may lead to less muscle soreness. Postural alignment of an individual's body may create optimum neurological and biomechanical feedback. Internal winding of an individual's hips may provide enhanced activation of the individual's glutes.

For the purposes of this disclosure, the terms "wind" or "wound", in conjunction with, or without the term "around", may be used interchangeably with the terms "wrap", "wraps around", "wrapped around", "affixed around", or "positioned around" when used in relation to a support structure 3,53,103,153,203 applied to garments 1,51,101,151,201 worn by an individual.

For the purposes of this disclosure, it is noted that a "midline", in reference to an individual's body or in reference to any of garments 1,51,101,151,201, may align with a sagittal plane that separates a left and right side of a garment wearer's body (runs from head to foot). It is further noted that, in embodiments, garments 1,51,101,151,201 are symmetrical in relation to the sagittal plane, unless otherwise noted.

For the purposes of this disclosure, the waistline (in reference to garment 1,51) may correspond with a transverse plane, which is a horizontal plane configured to divide an individual's body into an upper (superior) section and a lower (inferior) section. Furthermore, in embodiments, any portion of support structure 3,53 that wraps around hip section 7,57 can be considered to be below the waistline.

For the purposes of this disclosure, it is noted that the terms "directly connect" and "affixed to", in relation to form-fitting structure 2,52,102,152,202 and support structure 3,53,103,153,203 may refer to support structure 3,53, 103,153,203 being attached to form-fitting structure 2,52, 102,152,202 via an intervening layer or element (or, more specifically "attachment structure", in embodiments). As an example, intervening layers or elements may include, but are not limited to: adhesives, stitching, ultrasonic bonds, chemical bonds or thermal bonds.

For the purposes of this disclosure, it may be understood that when an individual is wearing garment 1,51,101,151, 201 support structures, 3,53,103,153,203 may act as a guidewire system that provides compression forces that are capable of mechanically restructuring joint movement in the individual (providing the individual with posture support). In addition, support structures 3,53,103,153,203 may allow for proper movement from an individual's hips.

For the purposes of this disclosure, it is noted that the term "appendage" generally refers to one or more of a pair of arms and legs of an individual, unless otherwise noted.

For the purposes of this disclosure, it may be understood that garments 1,51,101,151,201 may provide compression and/or postural/proprioceptive realignment to an individual's body. In relation to garment 1, garment 1 stabilizes an individual's back and forces the use of the individual's lower hips. In relation to garment 51, garment 51 winds an individual's legs to provide structural stability to posterior medially converging structure 66 located on back section 55. This configuration may provide support for the individuals back when extended and further provides proper back alignment.

In embodiments, first elastomeric segment 8/second elastomeric segment 21 and first elastomeric segment 58/second elastomeric segment 72 cross one another at crotch portions 14,64 directly below crotch portions 14,64 when an individual is wearing garment 1,51. In another embodiment, first elastomeric segment 8/second elastomeric segment 21 and first elastomeric segment 58/second elastomeric segment 72 cross one another at crotch portions 14,64 slightly rearward toward back sections 5,55 (closer to an individual's glutes) when an individual is wearing garment 1,51. The different configurations may provide increased comfort for an individual wearing garment 1,51, depending on the comfort preference of the individual.

In embodiments, support structures 3,53,103,153,203 may comprise varying widths either along a single support structure 3,53,103,153,203 or between multiple garments 1,51,101,151,201. Different widths of either portions or whole support structures 3,53,103,153,203 may adjust the overall tensioning forces applied to an individual's body when an individual is wearing any of garments 1,51,101, 151,201. For example, a thicker width of support structure 3,53,103,153,203 may lead to increased tensioning forces applied to an individual's body when an individual is wearing any of garments 1,51,101,151,201.

In embodiments, the elastomeric band body of any of support structures 3,53,103,153,203 is formed of an elastomeric fabric. In relation to this embodiment, a more seamless process of applying the support structures 3,53,103,153, 203 to the form-fitting portions 2,52,102,152,202 can occur. In additional embodiments, the elastomeric band body of any of support structures 3,53,103,153,203 is formed of a non-fabric, polymer (such as, but not limited to, latex or rubber).

In embodiments, support structures 3,53,103,153,203 may be sewn to respective form-fitting portions 2,52,102, 152,202 where support structures 3,53,103,153,203 are made of an elastomeric fabric material.

In an embodiment where the pair of lower appendage sections 15 of form-fitting portion 2 (garment 1) terminates at the upper legs, support structure 3 wraps around, and terminates at, the hips of an individual wearing garment 1. In an embodiment where the pair of lower appendage sections 65 of form-fitting portion 52 (garment 51) terminates at the feet, support structure 53 wraps around the upper and lower legs of an individual wearing garment 51 and terminates at the feet of the individual.

In embodiments, logos 19,70 may be affixed to respective form-fitting portions 2,52. In additional embodiments, logos 19,70 may be at least one of embroidered and printed. Depending on the fabric used for form-fitting portions 2,52, the construction means and materials used relating to logos 19,70 may vary. In additional embodiments, logos may also be affixed to at least one of leg garment 101, bra garment 151, or underwear garment 201 in any of the ways described above.

In embodiments, zip-front openings 20,71 may be affixed to respective front sections 4,54 of form-fitting portions 2,52. Zip-front openings 20,71 may assist an individual in making it easier to put on short-legged garment 1/long-legged garment 51. In additional embodiments, zip-front openings (not shown) may be affixed to respective front sections 104,154, 204 or back sections 105,155,205 of form-fitting portions 102,152, 202 of garments 101,151,201.

In embodiments, form-fitting portions 2,52,102,152,202 may comprise at least one of: spandex and elastane. In embodiments, support structures 3,53,103,153,203 may comprise a fabric. In additional embodiments, support structures 3,53,103,153,203 may comprise at least one of: spandex and elastane. In additional embodiments, form-fitting portions 2,52,102,152,202 may comprise a fabric while support structures 3,53,103,153,203 may comprise a fabric that includes a greater compressive strength than the fabric of the form-fitting portions 2,52,102,152,202.

In embodiments, form-fitting portions 2,52,102,152,202 may comprise a garment structure other than form-fitting (such as, for example, a loose fitting garment).

In embodiments, the width of support structures 3,53,103, 153,203 may be uniform throughout. In other embodiments, support structures 3,53,103,153,203 may decrease in width and/or thickness, and more specifically, may decrease in width and/or thickness along areas of curvature (around an individual's body). In additional embodiments, the width and/or thickness of support structures 3,53,103,153,203 may vary so that different widths and/or thicknesses of support structures 3,53,103,153,203 may match up with different portions of an individual's body when an individual is wearing one of garments 1,51,101,151,201. For example, the width and/or thickness of support structures in crotch portions 14,64,114 may be less than that found anywhere else along support structures 3,53,103 (which may increase comfort for an individual). As an additional example, increasing the width and/or thickness of at least a portion of any of support structures 3,53,103,153,203 may increase overall upward and downward compression forces on an individual's body when an individual is wearing any of garments 1,51,101,151,201.

It is noted that certain embodiments include potential advantages. Potential advantages in some embodiments may not be potential advantages in relation to other embodiments. Additionally, specific potential advantages in some embodiments are not necessarily required of all embodiments.

A plurality of additional features and feature refinements are applicable to specific embodiments. These additional features and feature refinements may be used individually or in any combination. It is noted that each of the following features discussed may be, but are not necessary to be, used with any other feature or combination of features of any of the embodiments presented herein.

Unless otherwise defined, all technical and scientific terms used herein have the same meanings as are commonly understood by one of ordinary skill in the art to which this disclosure belongs. Although methods similar or equivalent to those described herein can be used in the practice or testing of the present disclosure, suitable methods are described herein.

All publications, patent applications, patents, and other references mentioned herein are incorporated by reference in their entirety. In case of conflict, the patent specification, including definitions, will prevail. In addition, the materials, methods, and examples are illustrative only and not intended to be limiting.

It will be appreciated by persons skilled in the art that the present disclosure is not limited to what has been particularly shown and described hereinabove. Rather, the scope of the present disclosure is defined by the appended claims and includes both combinations and sub-combinations of the various features described hereinabove as well as variations and modifications thereof, which would occur to persons skilled in the art upon reading the foregoing description.

The invention claimed is:

1. A garment for supporting posture of an individual, the garment consisting essentially of: a form-fitting portion comprising an upper body section and a lower body section each having an interior surface area and an exterior surface area; an extra fabric layer comprising a support structure comprising an elastomeric band body, the support structure affixed to the exterior surface area of the form-fitting portion and positioned on an upper body section and a lower body section of the form-fitting portion; wherein the elastomeric band body comprises two separate contiguous pieces.

2. The garment of claim 1, wherein the support structure at least partially wraps around a first upper appendage section, a second upper appendage section, a first lower appendage section, and a second lower appendage section.

3. The garment of claim 2, wherein the support structure wraps around a first upper appendage section and a first lower appendage section in a first loop configuration and wraps around a second upper appendage section and a second lower appendage section in a second loop configuration.

4. The garment of claim 3, wherein the first loop configuration wraps around the first upper appendage section, extends across a back section of the form-fitting portion, and wraps around a first diagonally opposing lower appendage section of the first lower appendage section and the second lower appendage section, further wherein the second loop configuration wraps around the second upper appendage section, extends across the back section of the form-fitting portion, and wraps around a second diagonally opposing lower appendage section of the first lower appendage section and the second lower appendage section.

5. The garment of claim 3, wherein the first loop configuration converges with the second loop configuration at a first side midsection point and at a second side midsection point opposite the first side midsection point.

6. The garment of claim 3, wherein the first loop configuration and the second loop configuration are configured to propagate movement in a lower hip region of an individual when the individual is wearing the garment.

7. The garment of claim 2, wherein the support structure comprises a pair of tensioning devices each positioned along a respective one of the first upper appendage section and the second upper appendage section, the pair of tensioning devices configured to perform at least one of increasing and decreasing tension applied to an individual's body when the garment is worn by an individual.

8. The garment of claim 1, wherein the support structure comprises a first elastomeric segment extending medially from a first side of a shoulder section of the upper body section through a crotch portion of the lower body section and a second elastomeric segment extending medially from a second side of the shoulder section of the upper body section through the crotch portion of the lower body section.

9. The garment of claim 8, wherein the first elastomeric segment further extends in a spiral configuration along a first lower appendage section of the form-fitting portion and the second elastomeric segment further extends in a spiral configuration along a second lower appendage section of the form-fitting portion, further wherein the first elastomeric segment and the second elastomeric segment are configured to internally rotate hips of an individual, to hold the individual's back upright, and to pull the individual's shoulders back when the individual is wearing the garment.

10. The garment of claim 9, wherein each of the first elastomeric segment and the second elastomeric segment terminate at a respective one of a first loop end and a second loop end, each of the first loop end and the second loop end configured to wrap around a respective one of a first foot and a second foot of an individual to lift mid-arches of the first foot and second foot when an individual is wearing the garment.

11. The garment of claim 8, wherein the first elastomeric segment further extends through the crotch portion, wraps around a first front side of hip section of the lower body section, extends across the second elastomeric segment at a first side section, and extends across the upper body section to the first side of the shoulder section, further wherein the second elastomeric segment further extends through the crotch portion, wraps around a second front side of hip section of the lower body section, extends across the first elastomeric segment at a second side section, and extends across the upper body section to the second side of the shoulder section.

12. The garment of claim 8, wherein the first elastomeric segment and the second elastomeric segment cross one another at a convergence point at the crotch portion and extend laterally away from the convergence point along respective first and second lower appendage sections, further wherein the first elastomeric segment and the second elastomeric segment are configured to internally rotate hips of an individual, to hold the individual's back upright, and to pull the individual's shoulders back when the individual is wearing the garment.

13. The garment of claim 8, wherein the first elastomeric segment and the second elastomeric segment cross one another at the crotch portion, further wherein the first elastomeric segment and the second elastomeric segment are absent an attachment structure at the crotch portion, the attachment structure configured to directly connect support structure to form-fitting portion.

14. The garment of claim 1, wherein the support structure extends from a shoulder section of the form-fitting portion to a pair of foot sections of the form-fitting portion.

15. The garment of claim 1, wherein the elastomeric band body is formed of an elastomeric fabric.

16. The garment of claim 1, wherein the support structure comprises a first elastomeric segment wrapping around a front portion of a first upper appendage section, extending across an upper back section, and extending medially toward a midline of the garment, further wherein the support structure comprises a second elastomeric segment wrapping around a front portion of a second upper appendage section, extending across the upper back section, and extending medially toward the midline of the garment.

17. A garment for supporting posture of an individual, the garment consisting essentially of: a form-fitting portion comprising an upper body section and a lower body section each having an interior surface area and an exterior surface area; an extra fabric layer comprising a support structure comprising an elastomeric band body, the support structure affixed to the exterior surface area of the form-fitting portion and positioned on an upper body section and a lower body section of the form-fitting portion; wherein the elastomeric band body comprises two separate contiguous pieces.

18. The method of claim 17, wherein the affixing further comprises: affixing a first loop configuration of the support structure around a first upper appendage section of the form-fitting portion, across a back section of the form-fitting portion, and around a first diagonally opposing lower appendage section of the form fitting portion; and affixing a second loop configuration around a second upper appendage section of the form-fitting portion, across the back section of the form-fitting portion, and around a second diagonally opposing lower appendage section of the form-fitting portion.

19. The method of claim 17, wherein the affixing further comprises: affixing a first elastomeric segment extending medially from a first side of a shoulder section of the upper body section, through a crotch portion of the lower body section, and along a first lower appendage section of the lower body section in a spiral configuration;

and affixing a second elastomeric segment extending medially from a second side of the shoulder section of the upper body section, through the crotch portion of the lower body section, and along a second lower appendage section of the lower body section in a spiral configuration; wherein the first elastomeric segment and the second elastomeric segment are configured to internally rotate hips of an individual, to hold the individual's back upright, and to pull the individual's shoulders back when the individual is wearing the garment.

* * * * *